(12) United States Patent
Kadziela et al.

(10) Patent No.: US 6,829,362 B1
(45) Date of Patent: Dec. 7, 2004

(54) SOFT MOLDING COMPOUND

(75) Inventors: Vic Kadziela, New Britain, CT (US); Alan Litke, Waterbury, CT (US)

(73) Assignee: Henkel Corporation, Rocky Hill, CT (US)

( * ) Notice: Subject to any disclaimer, the term of this patent is extended or adjusted under 35 U.S.C. 154(b) by 136 days.

(21) Appl. No.: 10/081,564

(22) Filed: Feb. 22, 2002

(51) Int. Cl.$^7$ .................. H04R 25/00; C08L 75/14; C08L 75/16; C08F 2/46; C08J 3/28
(52) U.S. Cl. .............. 381/312; 29/896.21; 181/129; 181/130; 181/135; 381/328; 522/96; 522/174; 525/123; 525/127; 525/454; 525/455; 526/301
(58) Field of Search ............... 29/896.21; 181/129, 181/130, 135; 381/312, 328, 68, 68.6; 522/96, 174; 525/123, 127, 454, 455; 526/301

(56) References Cited

U.S. PATENT DOCUMENTS

| | | | |
|---|---|---|---|
| 4,375,016 A | * | 2/1983 | Harada .................. 181/135 |
| 4,439,600 A | * | 3/1984 | Moran, Jr. .............. 528/392 |
| 4,900,763 A | | 2/1990 | Kraushaar ............... 522/14 |
| 4,973,611 A | * | 11/1990 | Puder .................... 522/42 |
| 5,002,151 A | * | 3/1991 | Oliveira et al. .......... 181/130 |
| 5,185,234 A | * | 2/1993 | Nakatsukasa et al. .... 430/284.1 |
| 5,201,007 A | * | 4/1993 | Ward et al. ............. 381/328 |
| 5,401,806 A | * | 3/1995 | Braden et al. ........... 525/301 |
| 5,554,712 A | * | 9/1996 | Huynh-Tran et al. ..... 528/58 |
| 5,679,721 A | * | 10/1997 | Courtoy et al. .......... 522/95 |
| 5,763,503 A | * | 6/1998 | Cowperthwaite et al. ... 522/44 |
| 5,847,021 A | * | 12/1998 | Tortorello et al. ........ 522/90 |
| 5,916,669 A | * | 6/1999 | Parker et al. ........... 428/216 |
| 6,048,911 A | | 4/2000 | Shustack et al. ......... 522/96 |
| 6,107,361 A | * | 8/2000 | Tortorello et al. ........ 522/96 |
| 6,110,593 A | * | 8/2000 | Szum et al. ............ 428/383 |
| 6,387,976 B1 | * | 5/2002 | Flat .................... 522/96 |

FOREIGN PATENT DOCUMENTS

| | | |
|---|---|---|
| EP | 0 780 712 A2 | 6/1997 |
| EP | 0 849 296 A2 | 6/1998 |
| GB | 2 338 238 A | 12/1999 |
| WO | WO 01/27181 A1 | 4/2001 |

* cited by examiner

Primary Examiner—Rabon Sergent
(74) Attorney, Agent, or Firm—Steven C. Bauman

(57) ABSTRACT

A curable composition and method for producing a soft yet durable elastomeric in-the-ear product having a Shore A hardness of about 55 or less upon cure. The curable composition incorporated in a hearing aid apparatus provides a soft, flexible tip member which was mated to a rigid hearing aid shell. The tip member provides better comfort, durability and acoustic performance for a variety of ear canal shapes and movements. The curable composition which provides these properties includes a urethane acrylate oligomer and a reactive plasticizer or reactive diluent to provide a Shore hardness of about 55 or less upon cure. The curable composition may be used for other ear-worn products where these properties are desired like for ear plugs, ear phones and ear connectors.

24 Claims, 1 Drawing Sheet

SOFT MOLDING COMPOUND

BACKGROUND OF THE INVENTION

1. Field of the Invention

The present invention relates to a curable composition and method for producing a soft, yet solid elastomer in-the-ear product yielding the user greater comfort and durability. Additionally, the nature of the inventive soft body design provides better acoustic performance for a variety of ear canal shapes and various motion affecting the ear canal, such as head and jaw movements.

The present invention also provides for ear-worn configurations of subminiature electronic devices requiring discrete coupling to the ear. These devices include digital cellular telephone ear connections, ear plugs, headsets and ear phones for telecommunications, radio, television or computers.

2. Brief Description of Related Technology

Hearing aids need to be durable, comfortable and reliable. Durability focuses on the integrity of the material, long lasting, and integrity of the bonding of the components. Comfortability implies that the device is soft when placed in the ear canal. Reliability implies superior acoustic quality throughout the life of the device, which requires adequate sealing within the ear canal. The challenges to satisfy the comfort and reliability objectives are due to the dynamic nature of the ear canal, and the geometric alterations of the ear canal due to natural anatomical movement. The dynamic nature of the ear canal varies from person to person, and even the anatomical shape varies from ear to ear of the same person. The canal shape is geometrically altered by motion from the head and the mandible, usually causing elliptical elongation. These differences in canal shape and changes due to body movement make it difficult to achieve a comfortable and true acoustic seal.

Challenges in meeting comfort as well as durability are due to the nature of the ear canal and materials able to use. In the past, hearing aids were made from hard acrylic materials which have proven to be durable but uncomfortable. And when the device was displaced by motion, a leakage of sound pressure occurred. Attempts were made to use rubber instead of the hard acrylic materials, such as in U.S. Pat. No. 3,527,901 to Geib. Rubber is softer and more resilient than hard acrylic but it is not very comfortable and still lacks a true acoustic seal upon motion.

Attempt to use soft vinyl materials have also not been entirely successful in meeting the aforementioned characteristics. Although vinyl may be softer than rubber and offers a better acoustic seal, soft vinyl lacks durability, and in fact, after a relatively short period of time it shrinks, turns yellow and becomes hard or brittle. It is recommended in the hearing aid industry to replace vinyl components for behind-the-ear ear molds at least annually.

Silicone materials have also been used as the housing material, such as disclosed in U.S. Pat. No. 6,022,311 to Juneau, et al. The '311 patent discloses a two layer silicone housing bonded with an adhesive to the plastic faceplate of the device. Although silicone has a longer wear life than vinyl materials, it lacks strong bonding properties to the plastics commonly used in hearing aid instrumentality.

Polyurethanes have in the past been used for hearing aid components. For example, U.S. Pat. No. 5,763,503 to Cowperthwaite, et al. discloses a housing for an in-the-ear hearing aid made from a solid and stiff polyurethane, polyesters or polyether to support the instrumentality. The Shore D hardness is from 50 to 90. Polyurethane has been proven to provide a better acoustic seal than polyvinyl. The properties needed for the housing require a stiff, firm, harder material to support the instrumentality which conflict with the objective for softer, comfortable fit within the ear canal.

Thus, instead of focusing on the housing material attempts have been made to supply an attachment to the housing such as a covering or sleeve. This preserves the durability of the original housing material, while adding a comfort factor. For instance, U.S. Pat. No. 4,870,688 to Voroba, et al. discloses a soft, resilient covering which is affixed to the rigid bonding of the ear shell. No covering material or details on affixing the covering to the ear shell were disclosed. Another example, U.S. Pat. No. 5,002,151 to Oliveira, et al., discloses a disposable sleeve made of a soft polyurethane retarded recovery foam attached to the ear piece by mating of screw threads on the sleeve and the ear piece. Unfortunately, a sleeve concept would lack durability and require continual replacement. The sleeve creates a safety concern due to the possibility of this attachment to slip off from motion in the ear canal and possibly lodging in the ear canal. The inadequacy and quality of the disposable sleeves bond to the housing is a major concern.

Softer materials than the housing have been used to create a tip portion. The tip portion is a hollow body which extends into the canal for the acoustic signal to pass through. Some known examples follow.

U.S. Pat. No. 6,205,227 to Mahoney discloses a relatively flexible tip which is rigid enough to prevent collapse of the passageway for acoustic signals. The tip disclosed has protruding fins for a better fit and is attached to the housing by a snap or a screw for easy removal and replacement. No material for the tip was disclosed.

U.S. Pat. No. 5,201,007 to Ward et al. discloses an ear mold with an acoustic conduction tube inside and a flexible flanged tip. The flange is used to hold the tip in place within the canal. The ear mold is constructed of silicone, polyvinyl or soft acrylic. The tip is connected to the tube by adhesive or heating.

U.S. Pat. No. 4,375,016 to Harada discloses an ear tip having a bulbous tip portion with a sound delivery aperture and vents for apertures. The ear tip is constructed of vinyl, silicone, plastic or foam. No means of connecting the tip to the housing is disclosed.

The same inadequacies found in the attempts to make a soft sleeve are found in the attempts to make soft tips. The current material of construction for a soft tip offers more comfort and better acoustic delivery than the hard acrylic shell. Unfortunately, the tip is less durable due to the inadequate bonding properties of the tip material to the housing material. There exists a potential for the tip to become dislodged within the ear canal from the constant motion in the ear canal and strain on the adhesive bond or mechanical bond.

There is a need for a soft tip on a sufficiently rigid housing which is durable, long-lasting material and strong bonding properties; comfortable, soft enough; and reliable, superior acoustics. The prior attempts noted above at satisfying these properties were seemingly unsuccessful. The present invention meets these and other needs.

SUMMARY OF THE INVENTION

In one aspect of the invention, there is provided a curable composition which includes a urethane acrylate oligomer, a reactive plasticizer or reactive diluent and a cure system. The function of the reactive plasticizers or diluent is to lower the hardness of the curable composition to provide a softer composition having a Shore A hardness of about 55 or less once cured. Softness, as defined by the present invention, is represented by the Shore A durometer scale. Specifically, in the present invention softness is defined as having a Shore A of about 55 or less.

In another aspect of the invention, there is provided a curable composition of Shore A hardness of about 55 or less which includes di-functional urethane acrylate oligomer present in amounts of about 35% to about 43% by weight; mono-functional urethane acrylate present in amounts of about 15% by weight; a reactive plasticizer or diluent is present in amounts of about 35% to about 43% by weight; and a photoinitiator is present in amounts of about 5% by weight.

In another aspect of the invention, there is provided a composition which includes a reaction product of a urethane acrylate oligomer and a reactive plasticizer or diluent wherein the reaction product exhibits a Shore A hardness of about 55 or less.

In yet another aspect of the invention, there is provided a method of making a soft tip hearing aid component which includes the steps of: combining a curable composition, which includes urethane acrylate oligomer, a reactive plasticizer or diluent, and a cure system component; pouring the curable composition into a mold; and exposing the curable composition to photo-radiation for a time and intensity sufficient to cure the composition to a Shore A hardness of about 55 or less.

In still another aspect of the invention, there is provided a hearing aid component which includes a urethane acrylate oligomer, and a reactive plasticizer or diluent to lower the hardness, soften the cured composition to a Shore A hardness of about 55 or less.

In a final aspect of the invention, there is provided a hearing aid assembly which includes an amplifier means for receiving and amplifying unamplified sound; a tube adapted to conveying amplified sound from the amplifier means to a first end of the tube inside the ear canal; a soft tip enclosing the tube wherein the tip's composition includes a urethane acrylate oligomer, a reactive plasticizer or reactive diluent to decrease the hardness or soften the composition of the tip to a Shore A hardness of about 55 or less upon cure; and a housing comprising a cured monomeric material enclosing the amplifier means and the mating to the soft tip.

DETAILED DESCRIPTION OF THE PRESENT INVENTION

Figure 1:
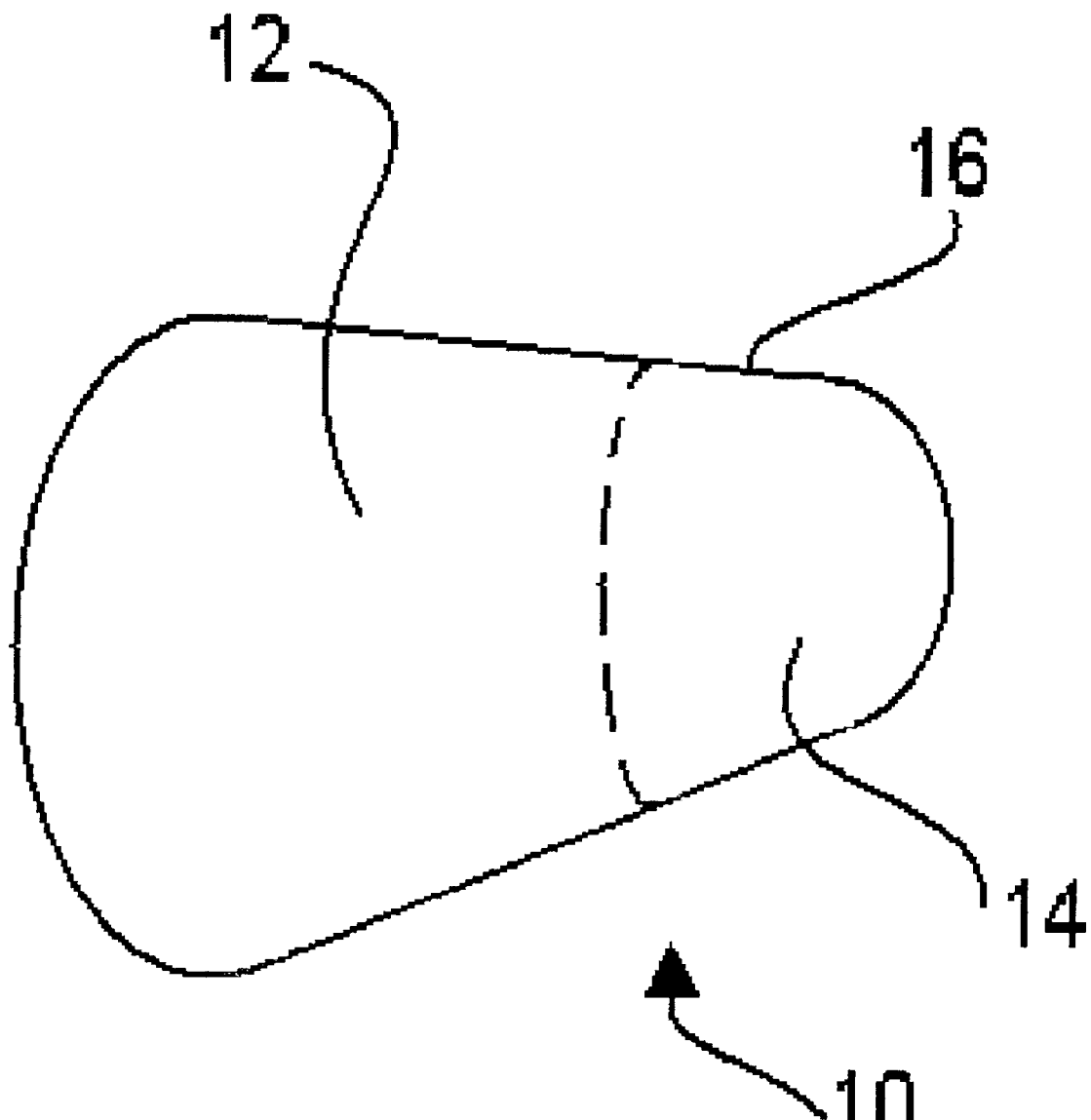
FIG. 1 shows a perspective view of a hearing aid housing attached to a soft tip according to the present invention.

As shown in FIG. 1, a hearing aid housing 12 of hearing aid assembly 10 is constructed to fit within the outer ear of the wearer. Adhesively, mated to the housing 12 is a soft tip 14 which projects through the concha and into the auditory canal area. The outer wall 16 of soft tip 14 forms a seal at the opening and in the auditory canal.

The hearing aid housing 12 typically contains amplifier means, volume adjustment control and battery access door, all of which are not shown. In operation, the amplifier means for receiving and amplifying unamplified sound is connected to a sound tube adapted for conveying sound from the amplifier means to the end of the tube inside the ear canal. The soft tip 14 encloses the tube for conveying sound and may contain other ports for various uses such as vent apertures. The end of the sound tube is positioned to deliver sound energy generally along the axis of the ear canal when inserted.

To provide a comfortable fit and an acoustic seal in the wearer's ear, soft tip 14 is formed of a curable composition which is deformable to assume the shape of the ear canal to provide an acoustic seal and be comfortable to the user. The sealing and comfort properties are important for commercial viability. Additionally, the inventive soft tip hearing aid components of the present invention are durable to provide long-lasting quality. The curable composition which forms the soft tip includes the reaction product of a urethane-acrylate component and a reactive plasticizer, designed to provide a Shore A hardness of about 55 or less.

Hardness Determination

Standard measurements of the hardness of various substances are currently performed using durometer hardness test procedures, such as those set forth in ASTM D2240 herein incorporated by reference. The durometer hardness procedures are used for determining indentation hardness of various substances, and are particularly useful for elastomeric materials. These test methods measure the depression force of a specific type of indentor as it is forced under specific conditions against the material's surface. Due to the various parameters which influence hardness determinations, different durometer scales have been established. A particular scale is chosen depending on the type of material to be measured. For example, materials which are relatively soft, such as elastomeric materials, are measured on a Shore A scale. Shore A scale measurements use a steel rod indentor shaped with a blunt end, and a calibrated spring force, as shown in FIG. 1 and Table 1, respectively of ASTM D2240. The indentor descends at a controlled rate against the specimen surface and a reading is recorded within a specified time period. This procedure is repeated multiple times at different positions on the specimen and the arithmetic mean of the results yields the Shore A measurement.

Durometer scales which are used for durometer hardness measurements include Shore A, B, C, D, DO, O, OO, and M. Each of theses scales has units from 0 to 100. There is no overlap between the scales, although certain materials may be suitable for testing on both scales. The geometry of the indentor and calibrated spring force scales influence the measurements, such that no simple relationship exists between the measurements obtained between different types of durometers. For example, the test for Shore D, which is designed for hardner materials, is distinct from Shore A in that the indentor is shaped with a pointed tip and the calibrated spring force has a higher force scale then Shore A. Generally, this test is not suitable for materials which are measured on a Shore A scale. A material having Shore D hardness, such as Cowperthwaite (Shore D from 50 to 90) is substantially different then the soft material of the present invention, which has a low Shore A value.

Urethane-Acrylate Compositions

The urethane-acrylate can be selected from a variety of materials, most desirable are materials to produce aliphatic urethane-acrylates. Useful urethane-acrylates include a di- or polyfunctionalized urethane-acrylate which is capable of cross-linking during cure and mono-functional monomers which are often incorporated as reactive diluents capable of copolymerizing with the various other polymerizable materials. When dealing with mono-functional urethane-acrylate, it is desirable to use an ester which has a relatively polar alcoholic moiety. Such materials are less volatile than low molecular weight alkyl esters and, more importantly, the polar group tends to provide intermolecular attraction during and after cure, thus producing more desirable cure properties, as well as a more durable sealant or adhesive. Particularly desirable are the polar groups selected from labile hydrogen, heterocyclic ring, hydroxy, amino, cyano, and halogen polar groups. Useful examples of compounds within this category include cyclohexyl (meth)acrylate, tetrahydrofurfuryl (meth)acrylate, hydroxyethyl acrylate, hydroxypropyl (meth)acrylate, t-butylaminoethyl (meth) acrylate, cyanoethylacrylate, and chloroethyl (meth) acrylate. Other unsaturated reactive diluents, such as styrene and acrylonitrile, can also be used.

Useful di- or polyfunctionalized urethane-acrylates include aliphatic polyester based urethane diacrylates. Other mono-, di-, or polyfunctional urethane-acrylate oligomers useful in the present invention can be described as the acrylated reaction product of an aliphatic alcohol, such as polycarbonate polyol, a polyether polyol, or ethylene glycol monoacrylate, and a polyisocyanate.

Representative polyether polyols useful in preparing the urethane-acrylate oligomers include straight or branched alkylene oxides having from one to twelve carbon atoms (C1–12), prepared by methods known in the art. Desirable, the polyether polyols have an average molecular weight, as determined by vapor pressure osmometry (ASTM-D 3592), sufficient to give the entire oligomer a molecular weight of about 6,000 daltons, desirably not more than 5,000 daltons and more desirably not more than 4,000 daltons. Examples include, without limitation; polytetramethylene polyol, polymethylene oxide, polyethylene oxide, polypropylene oxide, polybutylene oxide, tetrahydrofuran (THF)-sympolyether and combinations thereof.

Representative hydrocarbon polyols used to prepare the urethane-acrylate oligomers also include hydrocarbon polyols, straight or branched, having a molecular weight of from about 600 to 4,000. Non-limiting examples include fully or partially hydrogenated polybutadiene, polybutadiene hydrogenated to an iodine number of from 9 to 21, and fully or partially hydrogenated polyisobutylene.

Representative polycarbonate polyols used to prepare the urethane-acrylate oligomers include but are not limited to the reaction products of dialkyl carbonate with an alkylene diol, optionally copolymerized with alkylene ether diols.

The polyisocyanates used to prepare the urethane-acrylate oligomers include aliphatics and aromatics having from 4 to 20 carbon atoms (C4–20). Representative aliphatic examples include isophorone diisocyanate, dicyclohexylmethane-4,4'-diisocyanate, 1,4-tetramethylene diisocyanate, 1,5-pentamethylene diisocyanate, 1,6-hexamethylene diisocyanate, 1,7-heptamethylene diisocyanate, 1,8-octamethylene diisocyanate, 1,9-nonamethylene diisocyanate, 1,10-decamethylene diisocyanate, 2,2,4-trimethyl-1,5-pentamethylene diisocyanate, 2,2'-dimethyl-1,5-pentamethylene diisocyanate, 3-methoxy-1,6-hexamethylene diisocyanate, 3-butoxy-1,6hexamethylene, omega, omega'-dipropylether diisocyanate, 1,4-cyclohexyl diisocyanate, 1,3-cyclohexyl diisocyanate, trimethylhexylmethylene diisocyanate and combinations thereof.

Suitable catalysts for reacting the aliphatic alcohol with the polyisocyanate to form the urethane portion of the urethane-acrylate oligomers include such materials as: dibutyl tin dilaurate, dibutyl tin oxide, dibutyl tin di-2-hexoate, stannous oleate and octoate, lead octoate, ferrous acetoacetate; and amines, such as triethylamine, diethylmethylamine, triethylenediamine, dimethylethylamine, morpholine, N-ethyl morpholine, piperzine, N,N-dimethyl benzylamine, N,N-dimethyl laurylamine and combinations thereof.

The urethane oligomers thus formed are endcapped with a (meth)acrylate-containing group to form the urethane-acrylate. Suitable hydroxyl-terminated endcapping monomers include, without limitation, hydroxyalkyl (meth) acrylates, such as hydroxyethyl (meth)acrylate, hydroxypropyl (meth)acrylate, hydroxybutyl (meth) acrylate, and the like. Combinations of endcapping groups may be employed.

The molar ratio of the polyol, polysocyanate and endcapping monomer is desirably about 1:2:2, respectively.

Representative commercially available urethane-acrylate oligomers include: Sartomer CN 966J75, an aliphatic polyester based urethane diacrylate oligomer blended with 25% isobornyl acrylate; Sartomer CN-966H90, an aliphatic polyester based urethane diacrylate oligomer blended with 19% 2(2-ethoxyethoxy)ethyl acrylate; Sartomer CN-964, an aliphatic polyester based urethane diacrylate oligomer, Sartomer Company, Exton, Pa.; Aliphatic polyether based urethane diacrylate oligomer with hydroxyethyl acrylate, Loctite, Rocky Hill, Conn.; Rahn Genomer 1122, an aliphatic mono-functional urethane-acrylate with 2-hydroxyethylacetate, and urethane di-acrylates such as Genomer 4212, Genomer 4215, Genomer 4302, Genomer 4316, Hans Rahn & Co.

The di- and other polyfunctional urethane-acrylate oligomers of the present invention may be employed in amounts of about 25% to about 55% by weight of the total composition. The mono-functional urethane-acrylate monomers of the present invention may be employed in amounts of about 15% to about 65% by weight of the total composition. More desirably, the di-functional urethane-acrylate oligomer is present in amounts of about 30% to about 47% by weight of the total composition, and mono-functional urethane-acrylate monomer is present in amounts of about 10% to about 30% by weight of the total composition.

Reactive Plasticizer or Reactive Diluent

The reactive plasticizer may be selected from those materials known in the art which softens the urethane acrylate composition to exhibit a Shore A hardness of about 55 or less once cured. The reactive plasticizer may also be considered a reactive diluent, and may be either straight chained or branched, and should preferably be at least partially aliphatic. One type of reactive plasticizer which may be used is an alkyl acrylate, methacrylate or alkoxylated alkyl (meth) acrylate, having about 6–18 carbon atoms in the alkyl moiety of the molecule.

Desirably, the reactive plasticizer is an alkoxylated alkyl (meth)acrylate, such as 2(2-ethoxyethoxy)-ethyl acrylate (EOEOA). The reactive plasticizer may be introduced independently in the overall composition or in a pre-mix of oligomer.

Representative commercially available reactive plasticizers include Sartomer CN-966H90, an aliphatic urethane diacrylate oligomer blended with 19% 2(2-ethoyethoxy)-ethyl acrylate, Sartomer CN 966J75, an aliphatic polyester based urethane diacrylate oligomer blended with 25% isobornyl acrylate, and Sartomer SR-256, all from Sartomer, Exton, Pa.

The reactive plasticizer or diluent of the present invention may be employed in amounts sufficient to achieve the Shore A hardness values of about 55 or less, which generally is in amounts of about 0.5% to about 45% by weight of the total composition. More desirably, the reactive plasticizer is present in amounts of about 28% to about 45% by weight of the total composition. Even more desirably, the reactive plasticizer includes about 5% to about 10% 2(2-ethoxyethoxy)-ether acrylate by weight of the total composition.

Cure System Component

In applications where soft tips are to be made, the cure system is desirably one which is initiated by electromagnetic radiation. Photoradiation is most desirable for its ability to produce a well-controlled cure and high quality parts efficiently. Various photoinitiators, such as UV, visible and infrared may be employed.

The UV photo initiators are generally effective in the 200 to 400 mm range, and particularly in the portion of the spectrum which borders on the invisible light and the visible portion just beyond this, e.g. >200 $\mu$m to about 390 $\mu$m.

A variety of UV photoinitiators may be employed. Photoinitiators, those that will respond to UV radiation to initiate and induce curing of the (meth)acryl functionalized curable component, which are useful in the present invention include benzophenone and substituted benzophenones, acetophenone and substituted acetophenones, benzoin and its alkyl esters, xanthone and substituted xanthones, diethoxy-acetophenone, benzoin methyl ether, benzoin ethyl ether, benzoin isopropyl ether, diethoxyxanthone, chloro-thio-xanthone, N-methyl diethanol-amine-benzophenone, 2-hydroxy-2-methyl-1-phenyl-propan-1-one, 2-benzyl-2-(dimethylamino)-1-[4-(4-morpholinyl)phenyl]-1-butanone and mixtures thereof. Photoinitiators suitable for use in the present invention that will respond to visible light to initiate and induce curing include camphoroquinone peroxyester initiators and 9-fluorene carboxylic acid peroxyesters. Thermal initiators include 2,2'-azobisisobutyronitrile. The initiators set forth above are for the purposes of illustration only and are in no way meant to limit the initiators that may be used in the present invention.

Among the more desirable UV photoinitiators are oligo (2-hydroxy-2-methyl-1-4 (1-methylvinyl) propanone and 2-hydroxy-2-methyl-1-phenyl propan-1-one (monomeric) which is a mixture of oligomeric alpha hydroxy ketone and 2-hydroxy-2-methyl-phenyl 1-propane. It is sold under the name of Sartomer Esacure KIP-100F, Sartomer Corp., Exton, Pa.

Photoinitiators may be employed in amounts of about 1% to about 10% by weight of the total composition. More desirably, the photoinitiator is present in amounts of about 4% to about 7% by weight of the total composition.

Stabilizers and inhibitors may also be employed as well as chelating agents to control and prevent premature peroxide decomposition and polymerization. Among those useful inhibitors include phenols such as hydroquinone and quinones. Chelating agents may be used to remove trace amounts of metal contaminants. An example of a useful chelating agent is the tetrasodium salt of ethylenediamine tetraacetic acid (EDTA).

Other agents such as thickeners, plasticizers, fillers, elastomers, thermoplastics, dispersion stabilizers and other well-known additives may be incorporated where functionally desirable.

Various colorants can be included in the inventive compositions. The term "colorants" is used to include dyes, pigments and other materials which can be used to impart color to the composition. Dyes are generally water-soluble organics, which often become water-insoluble once cured. Pigments may be organic or inorganic materials and are generally in the solid form. In particular, the compositions of the present invention are designed to work particularly well with the more dense solid pigments which are available. These pigments, due to their density and insolubility, tend to drop out of the dispersion and form a sediment in compositions to which they are added. The present invention is designed to overcome this sedimentation tendency, keep such dense insolubles in dispersion for a longer period of time and provide for color homogeneity to be reestablished without substantial mixing.

Examples of useful pigments include, without limitation, white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange), ultramarine (blue, pink and violet), chrome-tin (pink) manganese (violet), cobalt (violet); orange, yellow and buff pigments such as barium titanate; cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide; manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black.

Combinations of pigments are generally used to achieve the desired color tone in the cured composition. Titanium and iron oxides in combination, are particularly useful in creating flesh tones for hearing aids, and tips.

The colorants may be present in the present invention in amounts sufficient to render the desired color. Desirably, colorants may be present in amounts of about 0.1 to about 10.0%, desirably about 0.2 to about 2.0% and more desirably in amounts of about 0.2 to about 0.6% by weight of the total composition Insoluble pigments are the desired form of colorant useful in the present invention.

Process of Making Soft Tip

The process of making the soft tip includes pouring the curable composition into the mold cavity of a light-penetrable mold, the mold having an exposed, generally upward-facing surface. The composition covers a major amount of the generally upward-facing surface and fills the majority of the cavity. The surface was then exposed to ultra-violet radiation through the transparent mold surface for a time and intensity sufficient to cure the composition to a Shore A hardness of about 55 or less. The composition was either completely cured, or a portion was cured to achieve a layer of cured composition having the shape of the cavity surface. The uncured composition above the cured material was then poured off to leave the cured tip. Depth of thickness of the tip was controlled using a combination of UV initiators, light intensity and time. Additional cure of the tip, if necessary, could also be achieved by exposing the tip to additional photoradiation from the open end of the cavity once the uncured liquid is removed.

The resulting tips are self-supporting, free from surface blemishes and uniform in color. They can be pigmented to match a variety of skin tones and are ideally suited for soft tip for hearing aid component.

The process of making the soft tip mated to the hearing aid housing includes pouring the curable composition into the lower portion of the mold cavity which is the tip cavity of a light-penetrable mold, the mold having an exposed, generally upward-facing surface. The composition fills the tip-cavity of the mold and covers a major amount of the generally upward-facing surface of the tip-cavity of the mold. The surface was then exposed to ultra-violet radiation through the transparent mold surface for a time and intensity sufficient to cure the composition to a Shore A hardness of about 55 or less. The composition was completely cured. An uncured monomeric material was poured on top of the cured tip into the top section of the mold cavity, the housing cavity. The uncured monomeric material covered a major amount of the generally upward-facing surface and filled the majority of the housing cavity. The surface was then exposed to ultra-violet radiation through the transparent mold surface to achieve a thin layer of cured monomeric material having the shape of the cavity surface. Above the cured monomeric material remained uncured composition, which was then poured off to leave the cured shell. Depth of thickness of the shell was controlled using a combination of UV initiators, light intensity and time. Additional cure of the shell, if necessary, could also be achieved by exposing the shell to additional photoradiation from the open end of the cavity once the uncured liquid is removed.

The resulting material is a cured hearing aid housing which is mated or adhered to one another by crosslinkage to the cured soft tip.

The following examples are intended to be non-limiting illustrations of compositions of the present invention.

EXAMPLES

Various urethane-acrylate compositions were prepared and tested for hardness. Table 1 sets forth nine inventive combinations and their associated Shore A hardness (STM- 707), all of which are about 55 or less. Table 1 shows the weight percent of each component of the inventive composition which includes: Urethane-Acrylate oligomer, further subdivided into mono-functional, di-functional and tri-functional; Reactive Plasticizer or Diluent; photoinitiator and the associated Shore A hardness.

TABLE 1

INVENTIVE COMPOSITIONS (% wt)

| COMPONENT | 1 | 2 | 3 | 4 | 5 | 6 | 7 | 8 | 9 |
|---|---|---|---|---|---|---|---|---|---|
| Urethane-Acrylate | | | | | | | | | |
| Mono-functional | 15.9 | 45.1 | 30 | 47 | 26.1 | 20.6 | 47 | 27.3 | 30 |
| Di-functional | 35.9 | 27.5 | 46.7 | 30 | 41 | 46.7 | 40 | 53.6 | 49.3 |
| Tri-functional | 0 | 9.8 | 0 | 0 | 0 | 0 | 0 | 0 | 0 |
| Reactive Plasticizer or Diluent | 43.2 | 21.3 | 18.7 | 18 | 28.6 | 28 | 8 | 14.9 | 15.7 |
| Photoinitiator | 5 | 6.1 | 4.6 | 5 | 4.3 | 4.7 | 5 | 4.2 | 5 |
| Hardness, Shore A | 40 | 43 | 45 | 50 | 50 | 50 | 55 | 55 | 55 |

Table 2 sets forth comparative urethane-acrylate compositions which are too hard, associated with a relatively high Shore A value, as compared to those of Table 1. These hardness values are not considered commercially viable because of both poor acoustic seal and overall discomfort

TABLE 2

SHORE A > 55, COMPOSITIONS (% wt)

| COMPONENT | 11 | 12 | 13 | 14 | 15 | 16 |
|---|---|---|---|---|---|---|
| Urethane-Acrylate | | | | | | |
| Mono-functional | 42 | 0 | 0 | 32.3 | 30 | 30 |
| Di-functional | 17 | 51.3 | 40 | 44.1 | 39.3 | 44.3 |
| Tri-functional | 20.5 | 0 | 0 | 3 | 10 | 5 |
| Reactive Plasticizer or Diluent | 14.8 | 43.7 | 55 | 15.6 | 15.7 | 15.7 |
| Photoinitiator | 5.7 | 5 | 5 | 5 | 5 | 5 |
| Hardness, Shore A | 58 | 60 | 75 | 75 | 80 | 80 |

As can be seen from Table 2, not all urethane-acrylate compositions are capable of producing a desired Shore A hardness of about 55 or less. For example, urethane-acrylate compositions with no mono-functional urethane acrylate are too hard, as seen in composition #12 and #13 of Table 2. As seen in Table 2, urethane-acrylate compositions with tri-functional urethane-acrylate tend to yield a hard composition as seen in compositions #11, #14, #15, #16 of Table 2. However, a urethane-acrylate composition containing a tri-functional urethane-acrylate can yield a softer composition, of about 55 or less, if sufficient mono-functional and reactive plasticizer is present in combination with the poly-functional urethane-acrylate, as seen in inventive composition #2 of Table 1.

The amount of mono-functional urethane-acrylate and reactive plasticizer needed to achieve the desired Shore A hardness in the cured composition may vary depending not only on the amount of polyfunctional urethane-acrylate, components used and the presence or absence of additional materials, such as tri-functional reactive plasticizers.

What is claimed is:

1. A curable composition comprising:
   (a) a urethane acrylate oligomer comprising at least one di- or poly-functional urethane acrylate monomer and at least one mono-functional urethane acrylate monomer;
   (b) a reactive plasticizer or reactive diluent; and
   (c) a cure system,
   wherein said composition when cured produces a Shore A hardness of about 55 or less.

2. The curable composition of claim 1, wherein said urethane acrylate oligomer comprises a di-functional urethane acrylate monomer present in amounts of about 25% to about 55% by weight of said curable composition.

3. The curable composition of claim 1, wherein said urethane acrylate oligomer comprises a di-functional urethane acrylate monomer present in amounts of about 30% to about 47% by weight of said curable composition.

4. The curable composition of claim 1, wherein said urethane acrylate oligomer comprises a mono-functional urethane acrylate monomer present in amounts of about 15% to about 65% by weight of said curable composition.

5. The curable composition of claim 1, wherein said urethane acrylate oligomer comprises a mono-functional urethane acrylate monomer present in amounts of about 10% to about 30% by weight of said curable composition.

6. The urethane acrylate of claim 1, wherein said reactive plasticizer or reactive diluent comprises a mono-functional (meth)acrylate.

7. The curable composition of claim 1, wherein said di- or poly-functional urethane acrylate comprises a polyester aliphatic urethane-acrylate.

8. The curable composition of claim 1, wherein said reactive plasticizer or reactive diluent is present in amounts of about 0.5 to about 45% by weight of said curable composition.

9. The curable composition of claim 8, wherein said reactive plasticizer or reactive diluent is present in amounts of about 28% to about 45% by weight of said curable composition.

10. The curable composition of claim 1, wherein said reactive plasticizer or reactive diluent is selected from the group consisting of 2(2-ethoxyethoxy)-ethyl acrylate, isobornyl acrylate and combinations thereof.

11. The curable composition of claim 1, wherein said cure system comprises a photoinitiator.

12. The curable composition of claim 11, wherein said photoinitiator is present in amounts of about 1% to about 10% by weight of the curable composition.

13. The curable composition of claim 11, wherein said photoinitiator is present in amounts of about 4% to about 7% by weight of the curable composition.

14. The curable composition of claim 1, further comprising a pigment selected from the group consisting of organic and inorganic pigments, dyes and combinations thereof.

15. The curable composition of claim 14, wherein said pigment composition is plasticized in a carrier.

16. A curable composition comprising:
   (a) a di-functional urethane acrylate oligomer, wherein said oligomer comprises about 35% to about 43% by weight of said curable composition;

(b) a mono-functional urethane acrylate, wherein said mono-functional urethane acrylate is present in amounts of about 15% by weight of said curable composition;

(c) a reactive plasticizer or reactive diluent, wherein said plasticizer or diluent is present in amounts of about 0.5% to about 43% by weight of said curable composition; and (d) a photoinitiator, wherein said photoinitiator is present in amounts of about 5% by weight of said curable composition, wherein said composition when cured produces a Shore A hardness of about 55 or less.

17. The curable composition of claim 16, wherein said reactive plasticizer or reactive diluent comprises 2(2-ethoxyethoxy)-ethyl acrylate present in amounts of about 5% to about 10% by weight of said curable composition.

18. A composition comprising the reaction product of:
(a) a urethane acrylate oligomer comprising at least one di- or poly-functional urethane acrylate monomer and at least one mono-functional urethane acrylate monomer; and
(b) a reactive plasticizer wherein said reaction product produces a Shore A hardness of about 55 or less.

19. A method of making a soft tip hearing aid component comprising the steps of:
(a) combining a curable composition comprising:
   (i) a urethane acrylate oligomer comprising at least one di- or poly-functional urethane acrylate monomer and at least one mono-functional urethane acrylate monomer;
   (ii) a reactive plasticizer or reactive diluent;
   (iii) a cure system;
(b) pouring said curable composition into a mold cavity of a mold; and
(c) exposing said curable composition to photo-radiation for a time and intensity sufficient to fully cure said composition to produce Shore A hardness of about 55 or less.

20. The method of claim 19, further comprising the steps of adding on top of said component a layer of uncured monomeric material and curing said monomeric material.

21. The method of claim 20, wherein said monomer material forms a hearing aid housing when cured.

22. The method of claim 21, wherein curing said monomeric material on top of said component includes adhering to one another.

23. An ear-worn hearing aid component comprising the reaction product of:
(a) a urethane acrylate oligomer comprising at least one di- or poly-functional urethane acrylate monomer and at least one mono-functional urethane acrylate monomer; and
(b) a reactive plasticizer or reactive diluent, wherein said composition when cured produces a Shore A hardness of about 55 or less.

24. A hearing aid assembly comprising:
(a) amplifier means for receiving and amplifying unamplified sound;
(b) a tube adapted for conveying amplified sound from said amplifier means to a first end of said tube inside the ear canal;
(c) a soft tip enclosing said tube comprising the reaction product of:
   (i) a urethane acrylate oligomer comprising at least one di- or poly-functional urethane acrylate monomer and at least one mono-functional urethane acrylate monomer; and
   (ii) a reactive plasticizer or reactive diluent,
   wherein said soft tip exhibits a Shore A hardness of about 55 or less; and
(d) a housing comprising a cured monomeric material enclosing said amplifier means and mating to said soft tip.

* * * * *

UNITED STATES PATENT AND TRADEMARK OFFICE
CERTIFICATE OF CORRECTION

PATENT NO. : 6,829,362 B1  Page 1 of 1
DATED : December 7, 2004
INVENTOR(S) : Kadziela et al.

It is certified that error appears in the above-identified patent and that said Letters Patent is hereby corrected as shown below:

Column 1,
Line 47, should read -- Attempts to use soft vinyl... --.

Column 5,
Line 40, should read -- ...3-butoxy-1,6-hexamethylene... --.

Signed and Sealed this

Twenty-eighth Day of June, 2005

JON W. DUDAS
*Director of the United States Patent and Trademark Office*